US006955669B2

(12) United States Patent
Curutcharry

(10) Patent No.: US 6,955,669 B2
(45) Date of Patent: Oct. 18, 2005

(54) TRANSFER SET IN PARTICULAR FOR DELIVERING A MIXTURE OF LIQUIDS FOR MEDICAL PURPOSES

(75) Inventor: Jean Curutcharry, Guethary (FR)

(73) Assignee: Technoflex, Bidart (FR)

( * ) Notice: Subject to any disclaimer, the term of this patent is extended or adjusted under 35 U.S.C. 154(b) by 0 days.

(21) Appl. No.: 10/250,976

(22) PCT Filed: Jan. 16, 2002

(86) PCT No.: PCT/FR02/00163

§ 371 (c)(1),
(2), (4) Date: Jul. 10, 2003

(87) PCT Pub. No.: WO02/056946

PCT Pub. Date: Jul. 25, 2002

(65) Prior Publication Data

US 2004/0116891 A1 Jun. 17, 2004

(30) Foreign Application Priority Data

Jan. 17, 2001 (FR) .................................. 01 00598

(51) Int. Cl.⁷ ...................... A61B 19/00; A61M 25/16; A61M 5/32; F16K 17/14; F16K 17/40
(52) U.S. Cl. ...................... 604/415; 604/533; 604/410; 604/537; 604/326; 137/797; 137/798; 222/541.4
(58) Field of Search ................................ 604/4.01, 6.16, 604/403, 408, 410, 415–416, 905, 523, 533, 604/537–39, 411–12, 414, 317, 322, 326, 604/264, 246–250; 128/898; 222/83, 541.1–541.4, 222/541.6; 285/3, 914–15, 304–305, 307, 285/312, 314, 80, 81, 93, 95, 394, 921; 251/12, 251/75, 85.5, 89, 142, 148–149, 153–155, 251/341–42; 137/67, 68.11, 68.14, 70, 797–9

(56) References Cited

U.S. PATENT DOCUMENTS

| 4,181,140 A | | 1/1980 | Bayham et al. |
| 4,294,250 A | * | 10/1981 | Dennehey .................... 604/403 |
| 5,393,101 A | * | 2/1995 | Matkovich ..................... 285/3 |
| 5,533,996 A | * | 7/1996 | Murphey et al. ........... 604/535 |
| 5,762,646 A | * | 6/1998 | Cotter ........................ 604/410 |
| 6,071,262 A | * | 6/2000 | Okamoto et al. ............. 604/82 |
| 2004/0015148 A1 | * | 1/2004 | Curutcharry ................ 604/414 |

FOREIGN PATENT DOCUMENTS

| EP | 0 363 770 | 4/1990 |
| FR | 2 468 059 | 4/1981 |
| WO | WO 99/44652 | 9/1999 |

* cited by examiner

Primary Examiner—Patricia Bianco
(74) Attorney, Agent, or Firm—Young & Thompson

(57) ABSTRACT

A transfer set in particular for delivering a mixture of liquids for medical purposes, from a so-called flexible main bag containing a first liquid and from at least a so-called auxiliary bag containing a second liquid, connectable to the main bag through a pair of Luer-Lock connectors respectively male and female. Each of the two connectors has, at one end, a frangible section engaged in the end of a tubing connected to one of the bags and, at the other end, elements for being coupled to the other connector, provided with elements for locking the connectors in coupled position. The invention is useful for delivering liquids for medical purposes.

3 Claims, 3 Drawing Sheets

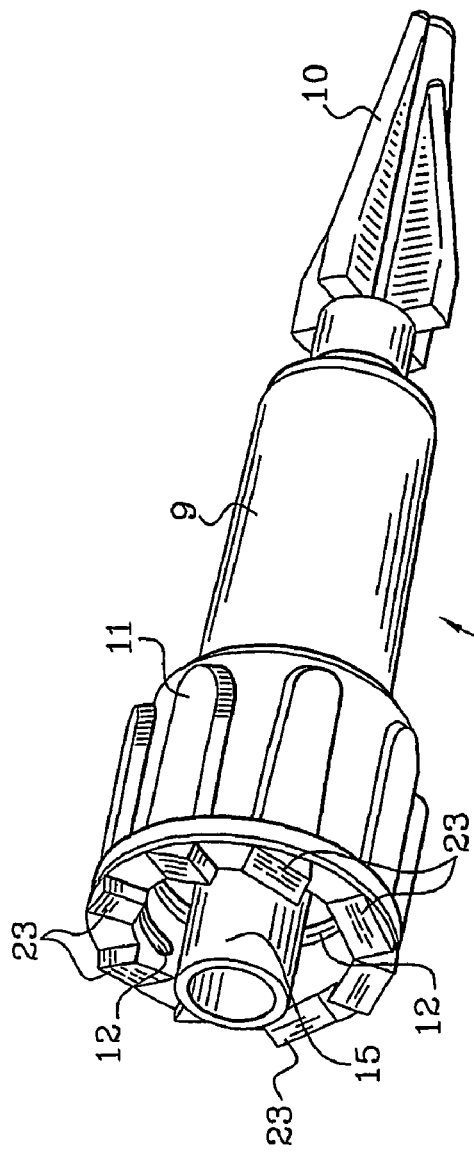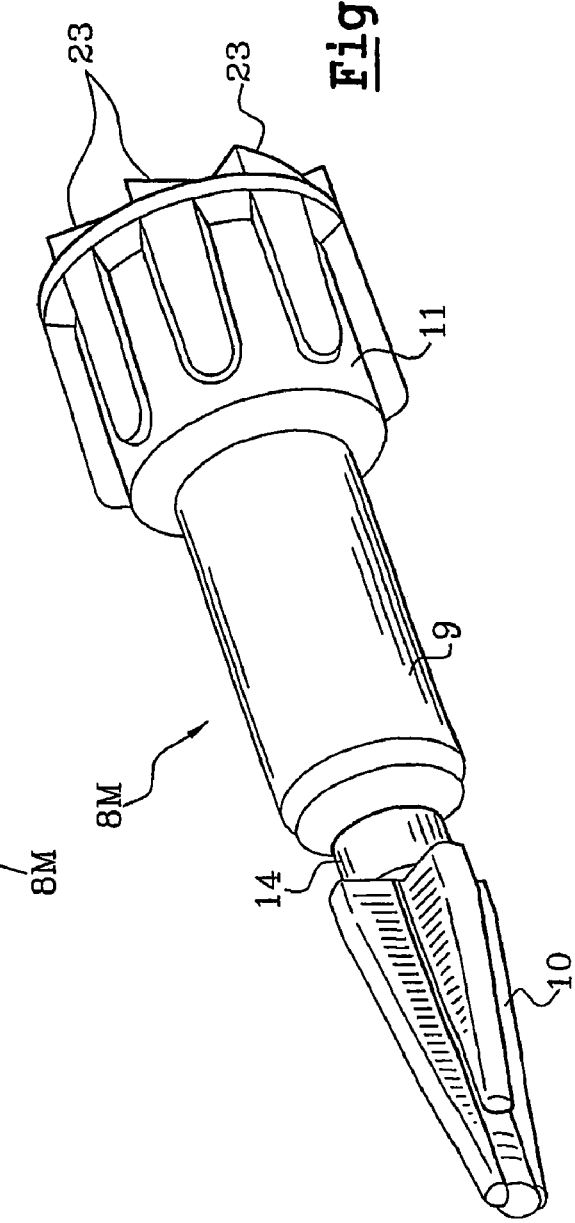

TRANSFER SET IN PARTICULAR FOR DELIVERING A MIXTURE OF LIQUIDS FOR MEDICAL PURPOSES

FIELD OF THE INVENTION

The invention relates more particularly, although not exclusively, to the administration for medical purposes of liquid substances, for example parenterally, from an assembly of flexible pouches comprising various liquid constituents to be mixed prior to administration.

BACKGROUND OF THE INVENTION

It is often necessary in such administrations to provide first, at the administration site, mixtures of measured quantities for example of one or several active principles with a diluent contained in a flexible pouch.

It is then necessary that an operator manually transfer the required quantities of active principles, for example with the help of a syringe, into the pouch of diluent, with all the risks of error from such a manipulation.

SUMMARY OF THE INVENTION

The present invention seeks to overcome these various drawbacks by providing a transfer set permitting carrying out extremely varied combinations of active principles under maximum conditions of safety, both for the patient and for the caregiver.

To this end, the invention has for its object a transfer set, particularly for the administration of a mixture of liquids for medical purposes, from a so-called principal flexible pouch containing a first liquid and at least one so-called auxiliary flexible pouch containing a second liquid, connectable to the principal pouch with the help of a pair of connectors of the mating type, respectively male and female, characterized in that each of the two connectors comprises, at one end, a frangible section engaged in the end of a tube connected to one of the pouches and, at the other end, coupling means to the other connector, provided with means for blocking in coupled position said connectors.

The device of the invention has the advantage of providing assemblies for administration that are ready to use, which is to say comprising a pre-connected principal pouch for example of diluent, which is to say connected to a tubular connection but not in communication, to a measured pouch or in parallel with several measured pouches of active principles or nutriments, and whose communication with the diluent pouch can be carried out in situ at any time and instantaneously by breaking the frangible sections of the connectors of the communication to be established.

The pre-connection in the sense defined above is carried out in a particularly certain manner because of the locking of the coupling of each pair of connectors, thereby ensuring a perfectly controlled asepsis and avoiding any cutaneous or aerial contact of the caregiver with potentially very active substances.

Such a pre-connection can of course be carried out at any time and particularly at the time of administration, by connecting to a principal pouch of diluent provided with one or several injection tubes in parallel each provided with a connector according to the invention, a suitably measured pouch provided with tubing having a complementary connector which is then coupled irreversibly to the connector of one of said injection tubes.

There is thus provided, by a simple, practical and rapid manipulation, the assurance of providing mixtures matching the prescriptions, by the choice of suitable pouch doses.

The possibility of providing pre-connections without communication permits packaging transfer sets that are ready to use, which can be easily stored and handled without risk.

The locked connection between the different pouches avoids any contamination, also during operations of trashing the pouches after use, because the assembly is eliminated without separation of the pouches.

Preferably, the pouches can be constituted by various materials suitable to the specific contents of the pouches, taking care to avoid possible container/content reactions.

The device of the invention is thus of great flexibility of use.

BRIEF DESCRIPTION OF THE DRAWINGS

Other characteristics and advantages will become apparent from the description which follows, of a preferred embodiment of the transfer set of the invention, which description is given by way only of example and with respect to the accompanying drawings, in which:

FIGS. 2a and 2b show two perspective views of a male element of the mating connector type according to the invention;

DETAILED DESCRIPTION OF THE DRAWINGS

Figure 1:
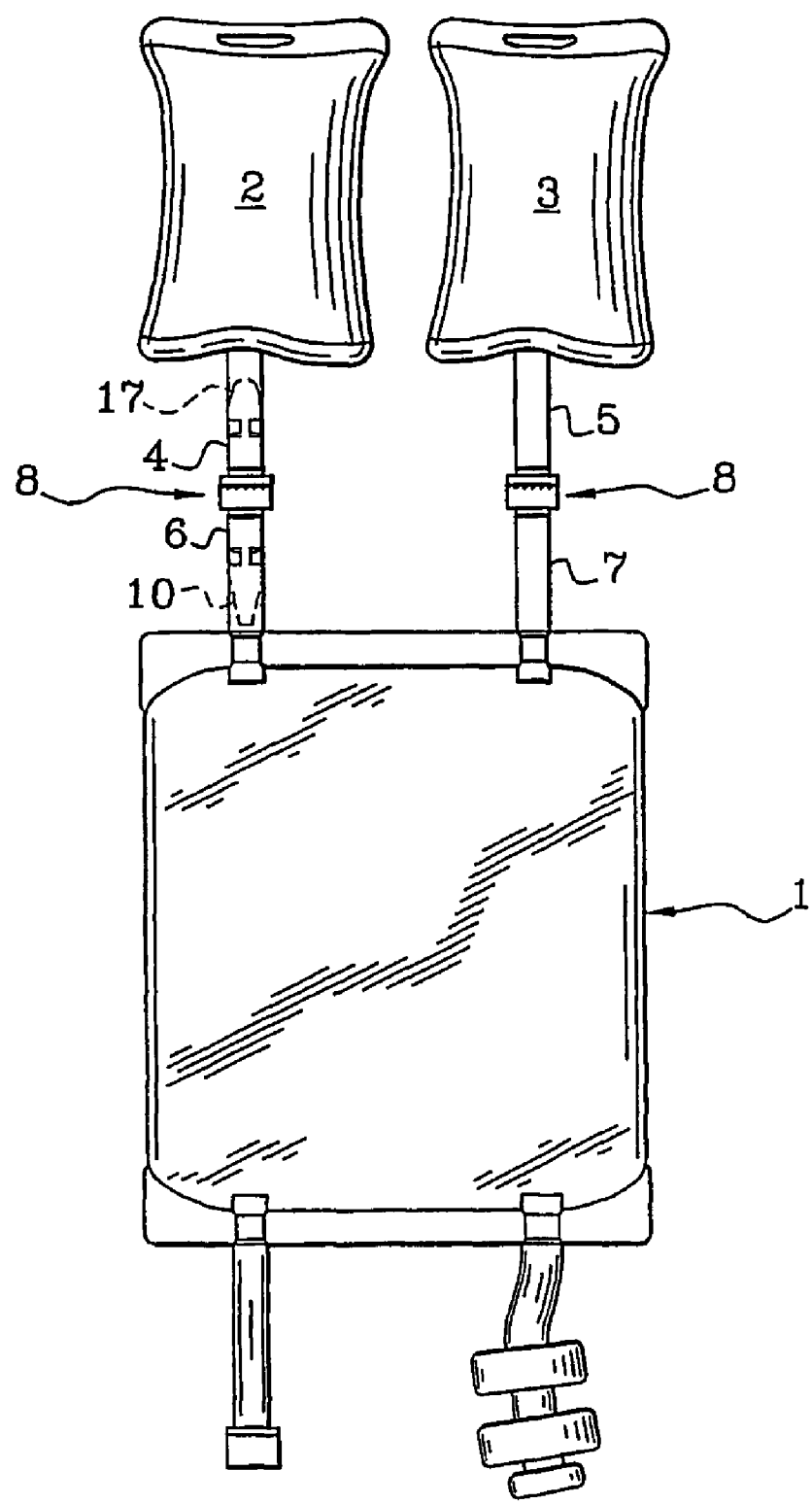
FIG. 1 shows schematically a transfer set according to the invention.
Figure 4:
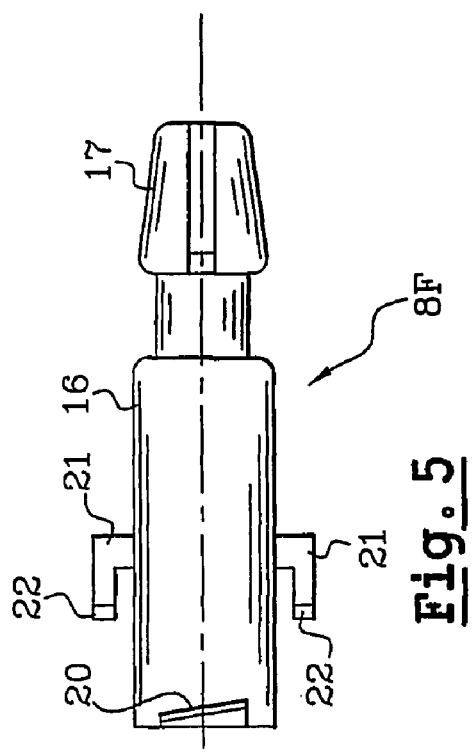
FIG. 4 is a side elevational view of a female mating connector element associated with the male elementn of FIG. 3.
Figure 5:
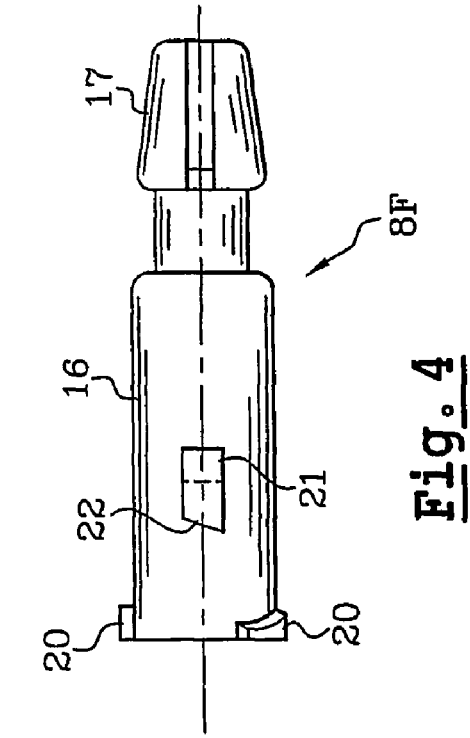
FIG. 5 is a view similar to that of FIG. 4, the female element having undergone rotation about its axis by 90°.

In FIG. 1 there is shown at 1 a so-called principal flexible pouch containing a first liquid, for example a solvent and at 2 and 3, two small separate pouches, called auxiliary pouches, containing for example two active principles of different composition, destined to be mixed with the solvent of pouch 1.

Each pouch 2, 3 comprises a tube, respectively 4 and 5, adapted to communicate with a tube respectively 6 and 7, connected to the pouch 1, via a connection of the male/female mating type 8, known per se.

FIGS. 2a, 2b, and 3 to 6 show an embodiment of two male and female elements according to the invention, of such a connection.

These elements comprise a connector of the frangible male mating type 8M (FIGS. 2a, 2b) and a connector of the frangible female mating type 8F (FIGS. 4, 5) provided with interconnection means.

The male mating connection 8M comprises a cylindrical body 9 prolonged at one end, in known manner, by a frangible section 10 of conventional shape, and at the other end by a cylindrical coupling collar 11 provided internally (FIG. 3) with a screw thread 12.

The body 9 is provided with a central passage 13 terminating, on the side of the frangible section 10, in a thin bridge 14 where the separation will take place between the section 10 and the body 9, while at its other end, the passage 13 communicates with a coaxial tubular portion 15 that slightly projects outside the collar 11.

Figure 3:
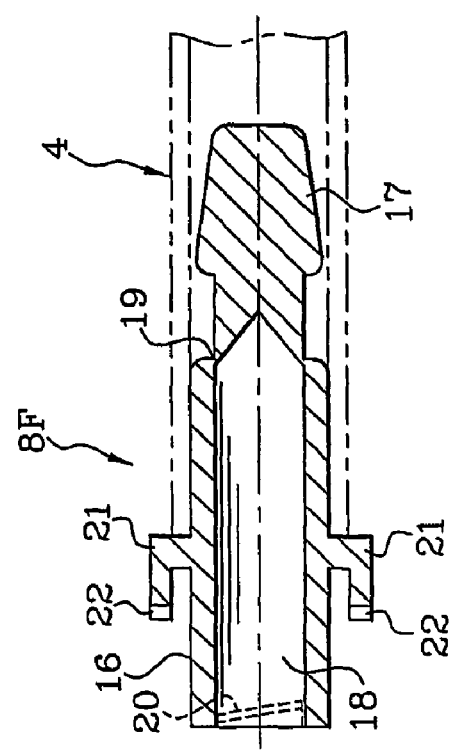
FIG. 3 is an axial cross-sectional view of the male element in place at the end of a connection tube.
Figure 6:
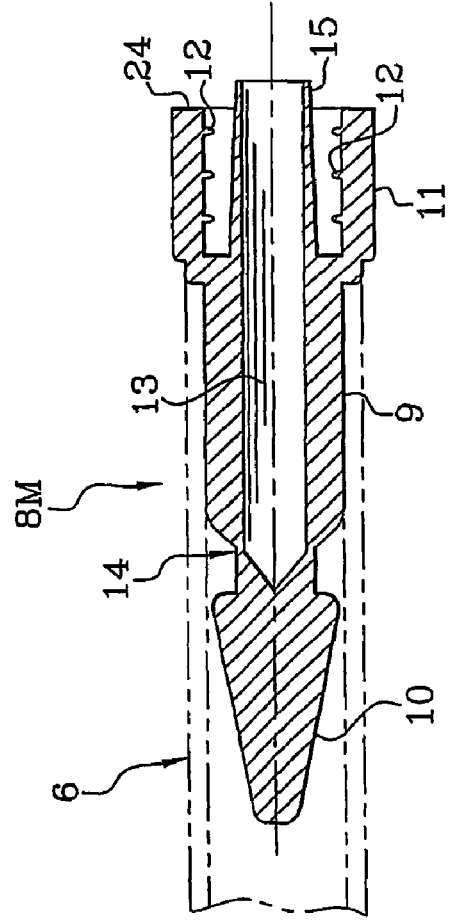
FIG. 6 is an axial cross-sectional view of the female element of FIG. 5.

As shown in FIG. 3, the male connection 8M is force-fitted into the end of the tube 6 for example, whose end comes into abutment against the collar 11 which has an external diameter substantially greater than that of the body 9 and corresponding substantially to that of said tube 6.

The female mating connector 8F comprises a cylindrical body 16 prolonged at one end and according to one characteristic of the invention, by a frangible section 17, of a type analogous to that of the male element 8M.

The body 16 has a cylindrical central passage 18 terminating on the side of the frangible section 17, adjacent a thin rupture bridge 19, analogous to bridge 14.

At its other end, the passage 18 is open and its diameter corresponds to the external diameter of the tubular portion 15 of the male connector 8M.

The female connector 8F is adapted to engage in the collar 11, the tubular portion 15 penetrating the passage 18.

Body 16 is provided externally opposite the frangible section 17, with two opposed screw-threaded sections 20, coacting with the screw thread 12 of the collar 11, so as to couple by screwing the male and female connectors 8M and 8F.

Preferably, the external wall of the tubular portion 15 is slightly conical to ensure sealing of the connection.

The female connector 8F is engaged (FIG. 6) in the end for example of the tube 4, in a manner similar to that of the male connector 8M, the frangible section 17 being within the tube 4 whose end, forcibly engaged on the body 16, comes into abutment against two diametrically opposed projections 21 on the exterior of body 16.

The projections 21 also define, on the side turned toward the male connector 8M, two inclined facets 22, adapted to coact with inclined complementary surfaces 23 provided circularly (FIG. 2a) on the section 24 of the collar 11, facing said facets 22.

The means 22, 23 constitute, according to the invention, a device of the snapping type and coact so as, at the end of screwing, to constitute a non-return dog constructions preventing unscrewing of the assembled connectors.

The two connectors 8M, 8F can be coupled at any time, for example to emplace a measured flexible pouch 2 on a pouch 1 and thereby to prepare a mixture of the contents of measured pouch 2 with that of pouch 1, which mixture could be carried out ultimately at any time by simple rupture of the bridges 14 and 19 of the connectors 8M and 8F of the abutting connection 8.

The pouches 2 and 3 can of course contain dosages that are different or not, of products that are different or not.

Preferably, the male connector 8M will be engaged in the tube (6, 7) secured to the pouch 1.

It is clear that a same principal pouch 1 can comprise several transfer tubes such as 6 or 7, not connected to measured pouches 2, 3, which is to say on hold, these tubes being provided for example with a male connector 8M.

Any measured pouch comprising a tube such as 4, 5, provided with a female connector 8F, can at any time be connected to the pouch 1 and placed in communication with the latter, immediately or later.

There is thus the assurance of a suitable mixture of measured quantities, thanks to the set of measured pouches provided according to the invention.

It is also to be noted that a set constituted by a principal pouch 1 and one or several measured auxiliary pouches 2, 3 can thus be packaged and stored in sterile packaging, the connections 8 being in place with the frangible sections 10, 17 of course not ruptured.

The principle of the transfer set according to the invention gives the possibility of packaging the solvent and the active principles according to completely disjointed and different industrial processes.

To this end, the materials of the various pouches can be adapted to the products to avoid possible container/content reactions.

The connections between pouches are completely safe because of the irreversible character of the assembly of the male and female elements 8M and 8F, from which results a perfectly controlled asepsis, any cutaneous or aerial contact of the caregiver with the potentially very active substances being avoided.

Any communication is also avoided after use, because it is the assembly of the set which is trashed, without separation of the pouches.

The transfer set of the invention is applicable generally to the production of measured mixtures particularly in the field of the administration of liquid substances for nutritional, chemotherapy, antibiotic therapy, etc., from an assembly of flexible pouches containing various measured substances which are to be mixed before administration.

Finally, the invention is obviously not limited to the embodiment shown and described above, but on the contrary covers all the variants, particularly as to the arrangement to carry out the coupling in an irreversible manner, between the male and female connectors.

What is claimed is:

1. Transfer set particularly for the administration of a mixture of liquids for medical purposes, comprising a pair of connectors comprising respectively male (8M) and female (8F) mating connectors, wherein each of the two connectors (8M, 8F) comprises, at one end, a frangible section (10, 17) engaged in the end of a tube (6, 4) and, at the other end, means (11, 12, 20) for coupling to the other connector, and means (22, 23) for blocking in coupled position said connectors (8M, 8F).

2. Transfer set according to claim 1, wherein said blocking means are constituted by means of the non-return snap type (22–23) arranged on the two portions adapted to be coupled (19, 16) of the connectors (8M, 8F).

3. Transfer set according to claim 1, in combination with a principal flexible pouch (1) containing a first liquid and at least one auxiliary flexible pouch (2, 3) containing a second liquid, said connectors interconnecting said pouches and providing liquid communication between said pouches upon breaking of said frangible sections (10, 17).

* * * * *